United States Patent [19]

Namekawa

[11] Patent Number: 4,759,375
[45] Date of Patent: Jul. 26, 1988

[54] ULTRASONIC DOPPLER DIAGNOSTIC APPARATUS

[75] Inventor: Kouroku Namekawa, Tokyo, Japan

[73] Assignee: Aloka Co., Ltd., Tokyo, Japan

[21] Appl. No.: 947,027

[22] Filed: Dec. 22, 1986

[30] Foreign Application Priority Data

Dec. 26, 1985 [JP] Japan ................ 60-292109
Dec. 26, 1985 [JP] Japan ................ 60-292112

[51] Int. Cl.$^4$ ............................................. A61B 10/00
[52] U.S. Cl. ................................... 128/663; 73/861.25
[58] Field of Search ............................. 128/660–663;
73/861.25; 367/90

[56] References Cited

U.S. PATENT DOCUMENTS

| | | | |
|---|---|---|---|
| 4,265,126 | 5/1981 | Papadofrangakis et al. | 73/861.25 |
| 4,336,808 | 6/1982 | Ohno et al. | 128/663 |
| 4,573,477 | 3/1986 | Namekawa et al. | 128/663 |
| 4,583,409 | 4/1986 | Lannuzel et al. | 128/663 X |
| 4,622,977 | 11/1986 | Namekawa et al. | 128/663 |
| 4,671,294 | 6/1987 | Magnin et al. | 128/663 |

Primary Examiner—Francis J. Jaworski
Attorney, Agent, or Firm—Koda and Androlia

[57] ABSTRACT

An ultrasonic Doppler diagnostic apparatus usable for ultrasonic image diagnostics accurately determines and displays the velocity of moving reflective members within a subject under observation by transmitting an ultrasonic beam into the subject and receiving the echoes reflected by the moving reflective members. The apparatus comprises a memory for storing a first velocity distribution obtained from a first signal received from a given direction, and a tangential velocity calculator for calculating a tangential velocity distribution in a direction tangential to an arc of a scanned sector by comparing said first velocity distribution within a second velocity distribution obtained from a second signal received from a direction deflected by a small angle with respect to the direction of the first signal. When the apparatus is to be adapted for determining velocity by the autocorrelation method, it is provided with a memory for storing a first autocorrelation signal output by an autocorrelator and a tangential velocity calculator for calculating the tangential velocity distribution from the first autocorrelation and a second autocorrelation having a slightly different angle of deflection.

The vectorial velocity of the moving reflective body is determined from the tangential velocity obtained by the tangential velocity calculator so that it is easily possible to obtain accurate velocity information including movement direction information with respect to the moving reflective member without need of transmitting ultrasonic beams from two separated locations. The apparatus thus provides accurate and useful information for use in image diagnostics.

8 Claims, 6 Drawing Sheets

ULTRASONIC DOPPLER DIAGNOSTIC APPARATUS

BACKGROUND OF THE INVENTION

1. Field of the Invention

This invention relates to an ultrasonic doppler diagnostic apparatus, more particularly to an ultrasonic Doppler diagnostic apparatus capable of computing the velocity of movement of a moving reflective member within a subject under observation and accurately displaying such movement.

2. Description of the Prior Art

The ultrasonic pulse-Doppler method has been practically applied in the measurement of the velocity of movement of a body organ such as the heart, of blood flowing in the blood vessels, of other body fluids, or of the cardiac muscles. The velocity of movement is detected from the frequency shift of an echo reflected from the moving member within the subject.

The applicant previously filed an application for patent on a Doppler apparatus of this type constituted as a velocity computing apparatus based on autocorrelation, and this application was allowed as U.S. Pat. No. 4,573,477.

In the patented apparatus, the Doppler signal received from within the subject is converted to complex signals, autocorrelation of the complex signals is determined, and the frequency shift is computed from the autocorrelation value. The frequency shift obtained in this manner corresponds to the velocity of the moving reflective member so that it is possible to determine the velocity of the moving reflective member with high accuracy from the magnitude of the frequency shift.

The apparatus further displays the velocity of the moving reflective member on a CRT (cathode ray tube) in either B mode or M mode, in this way providing useful information for use in diagnosis through visual images.

When an ultrasonic Doppler apparatus employs only a single beam, however, accurate measurement of the velocity of moving a reflective member can be realized only for movement radial to the direction of the ultrasonic beam.

Because of this, it has been the practice to direct a plurality of beams originating from somewhat separated locations into the subject and then to obtain velocity information that includes the direction of movement of the moving reflective member by synthesizing the so-obtained plurality of velocity signals.

However, this method is disadvantageous not only in that it requires an apparatus of complex structure but also in that it cannot be applied when the moving reflective member is such that the transmission of the beams into the subject can be carried out only from limited locations or at a narrow range of angles. This problem arises particularly, for example, when the moving reflective member under observation is a cardiac muscle or the like.

SUMMARY OF THE INVENTION

In view of the above-mentioned disadvantages inherent in conventional apparatuses, the object of the invention is to provide an ultrasonic Doppler apparatus capable of producing accurate velocity information including movement direction information with respect to a moving reflective member by simple scanning and without need of transmitting ultrasonic beams from more than one location.

In order to attain this object, the present invention provides an improved ultrasonic Doppler diagnostic apparatus of the type wherein an ultrasonic pulse beam of a given fixed pulse-recurrence frequency (pulse rate) is transmitted into a subject and detection of the distance to the moving reflective member and the velocity of the moving reflective member are detected by comparing transmitted and received signals, the improvement comprising provision of the ultrasonic doppler diagnostic apparatus with a memory for storing velocity distributions and a tangential velocity calculator.

The apparatus according to the invention is characterized in that the memory stores a first velocity distribution produced by a velocity calculator on the basis of a first received signal from a first arbitrarily selected direction and the tangential velocity calculator computes a tangential velocity distribution component by comparing the first velocity distribution with a second velocity distribution obtained from a second received signal having a slightly different angle of deflection from the first received signal.

Another feature is that the apparatus can carry out velocity calculation by the autocorrelation method using a complex signal converter and an autocorrelator. In such case, the Doppler signal received from the subject is first converted into a complex signal by mixing it with a pair of complex reference signals which are complexly related to each other and which have frequencies that are integer multiples of the transmission pulse rate. Then the autocorrelation is obtained from this complex signal, whereafter the frequency shift, which constitutes the velocity component, is computed from the autocorrelation value.

To enable such operation, the apparatus according to the invention is provided with a line memory capable of simultaneously storing the velocity of a moving reflective member in arbitrarily selected directions, a tangential velocity calculator and a vector calculator. More specifically, the line memory stores a first autocorrelation output obtained based on a first signal received from an arbitrary selected direction and the tangential velocity calculator compares the first autocorrelation output with a second autocorrelation output obtained from a second received signal having a slightly different angle of deflection from the reception angle of the first received signal, in this way successively computing the tangential velocity over a sector scanning arc. Another feature of the invention is that the vector calculator uses the output of the tangential velocity calculator to calculate a vectorial velocity including the direction of movement of the moving reflective member.

With the aforesaid arrangement, the tangential velocity component is obtained by comparing the first velocity distribution stored in the memory with the second velocity distribution obtained for a received signal having a slightly different angle of deflection from the first received signal. This tangential velocity represents the velocity changes occurring in the tangential direction at a given distance within the subject. Therefore, from this tangential velocity and the radial velocity relative to the direction of transmission of the ultrasonic beam it is possible to obtain the vectorial velocity, that is to say the absolute velocity, and the vector angle.

Also, with an arrangement using the autocorrelation method, it is possible to obtain the tangential velocity by comparing the first autocorrelation signal stored in the line memory with a second autocorrelation signal having a slightly different angle of deflection from the first autocorrelation signal. Then, from the so-obtained tangential velocity it is possible to obtain the absolute velocity of the moving reflective member as well as the vector angle.

Therefore, since this vector angle indicates the direction of movement of the moving reflective member and, further, since this vector angle including the direction of movement can be obtained with respect to the entire velocity distribution within one and the same beam as well as for the entire region of ultrasonic beam transmission and reception, the arrangement of the invention enables accurate visual display of the velocity and direction of movement of the moving reflective member.

DESCRIPTION OF PREFERRED EMBODIMENTS

Figure 1:
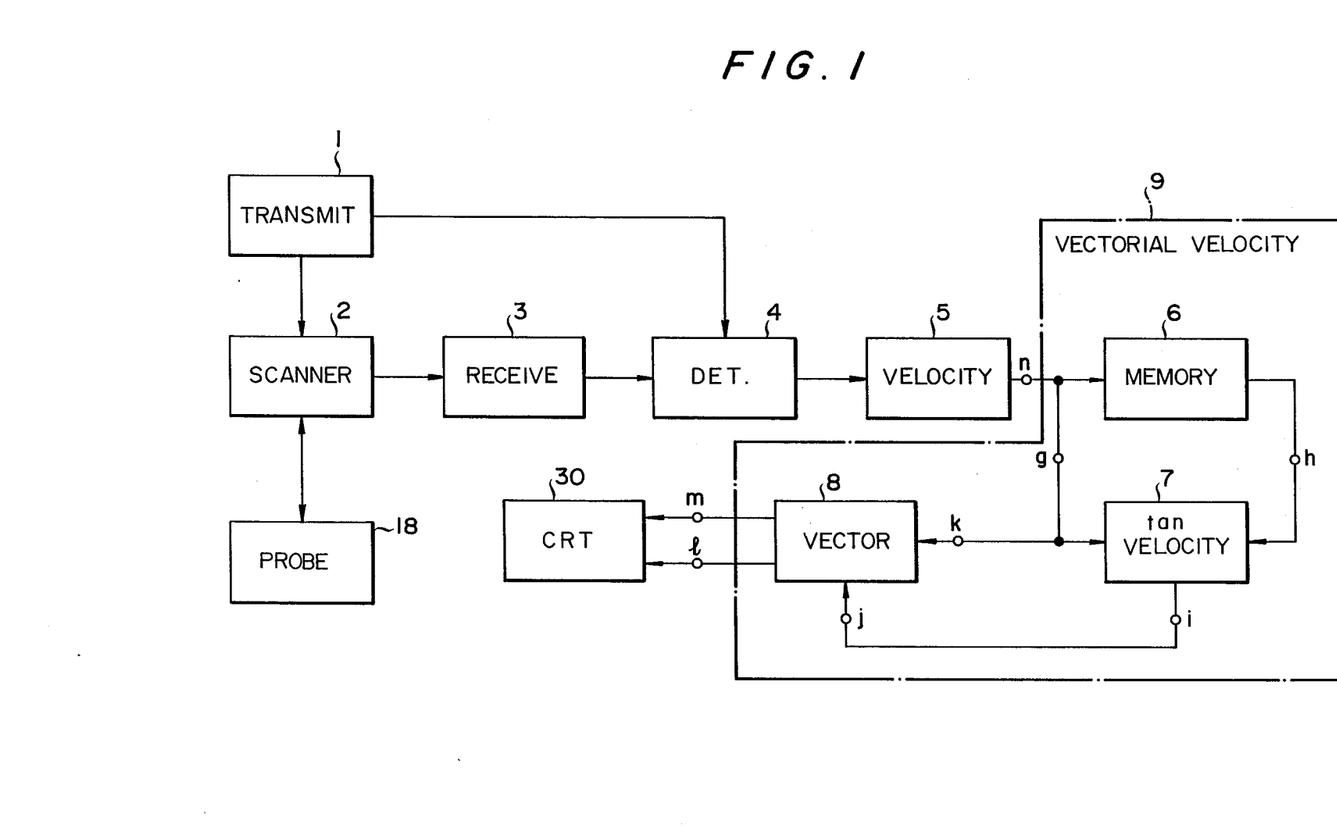
FIG. 1 is a block circuit diagram of a first embodiment of the ultrasonic Doppler diagnostic apparatus according to the invention.

FIG. 1 shows a block diagram of a first embodiment of the ultrasonic Doppler diagnostic apparatus according to the invention. A transmitter 1 outputs pulses to an electronic scanner 2 at a given fixed pulse-recurrence frequency (pulse rate). The electronic scanner 2 controls a probe 18, providing beam deflection control in the case of sector scanning, and, as a result, an ultrasonic pulse beam is transmitted in the selected direction by the probe 18.

The probe 18 is brought into contact with the surface of the subject and the ultrasonic pulse beam is radiated into the interior of the subject. At this time, echo signals arising from a moving reflective member within the subject are received by the probe 18 and then sent to a receiver 3 via the electronic scanner 2. The receiver 3 amplifies the received ultrasonic signal and sends it to a detector 4 where the received signal is mixed with a reference wave having a pulse rate that is an integer multiple of the pulse rate of the pulses output by the transmitter 1, whereupon the received ultrasonic signal is detected.

The output of the detector 4 is supplied to a velocity calculator 5 which converts the analog signal to a digital signal and then carries out computation to produce a velocity signal.

What characterizes the present invention is that the velocities of two received signals having a slight difference in deflection angle are compared so as to obtain the difference velocity, i.e. the tangential velocity, at the same distance and that the vectorial velocity is calculated from this tangential velocity. For this purpose, this first embodiment is provided with a vectorial velocity calculator 9 consisting of a memory 6 for storing a first velocity distribution of a first received signal to be subjected to comparison, a tangential velocity calculator 7 for comparing the first velocity distribution and a second velocity distribution of a second received signal so as to obtain the tangential velocity, and a vector calculator 8 for carrying out vector calculation on the basis of the output of the tangential velocity calculator 7. Here the memory 6 serves to delay the first velocity distribution by a predetermined period of time so that it can be compared with the second velocity distribution. In this invention, the means used for such delay need not necessarily be a memory but may alternatively be any of various types of delay lines. The vector calculator 8 is connected to a CRT display 30.

Figure 2:
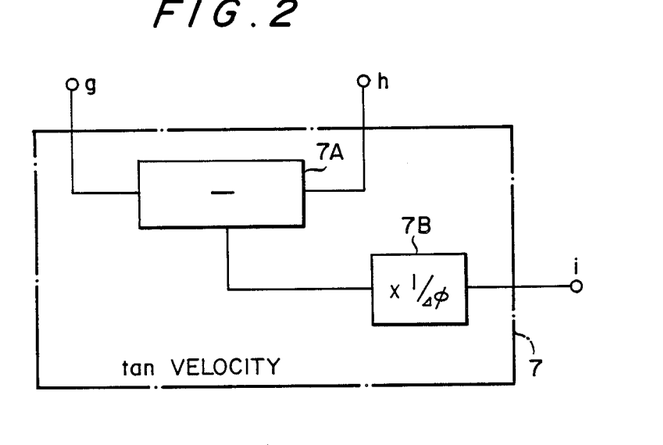
FIG. 2 is a block diagram showing the circuit arrangement of a tangential velocity calculator in the embodiment of FIG. 1.

FIG. 2 shows the circuit arrangement of the tangential velocity calculator 7. It consists of a subtractor 7A for calculating the differences between inputs applied to terminals g and h, and a multiplier 7B for multiplying this difference by $1/\Delta\phi$.

Figure 3:
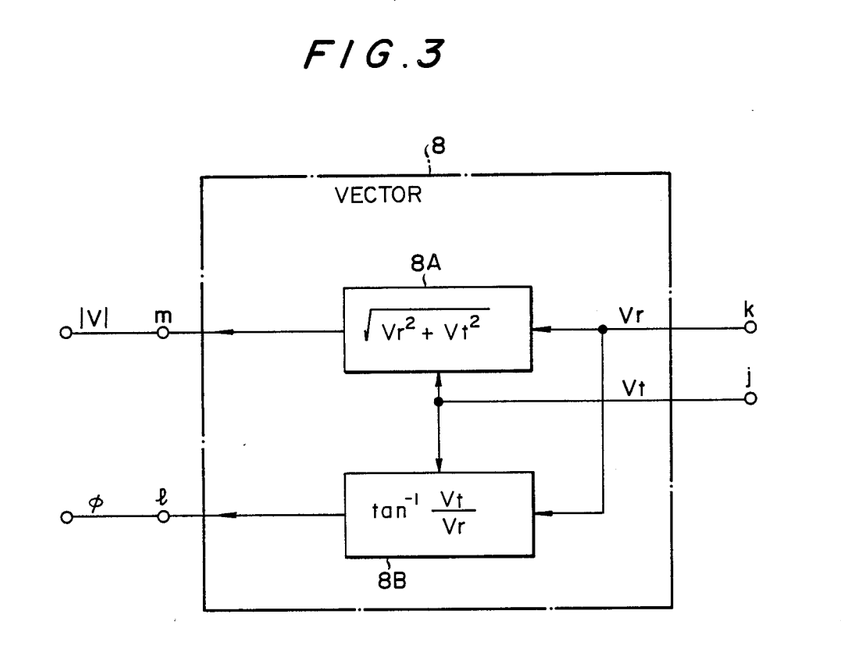
FIG. 3 is a block diagram showing the circuit arrangement of a vector calculator in the embodiment of FIG. 1.

As shown by FIG. 3, the circuit of the vector calculator 8 consists of an absolute value calculator 8A for calculating the absolute velocity from the tangential velocity and a vector angle calculator 8B for calculating the vector angle.

The operation of the invention constituted as described above will now be explained with reference to FIGS. 4 and 5.

Figure 4:
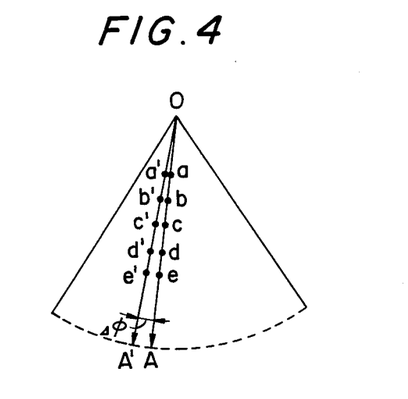
FIG. 4 is a diagram for explaining the relationship between two received signals of slightly different angles.

First, as shown in FIG. 4, if the ultrasonic beam is radiated from point O toward point A, there will be obtained echoes from, for example, points a, b, c, d, and e. The signal received from the OA direction will be referred to as the first received signal. In this case, if the ultrasonic pulse wave is transmitted a plurality of times signals $a_1, a_2, a_3 \ldots, b_1, b_2, b_3 \ldots, c_1, c_2, c_3 \ldots$ will be obtained and from these the velocity calculator 5 calculates the average velocities Vra, Vrb . . . Vre at the respective points. Then this velocity distribution in the OA direction, which will be referred to as the first velocity distribution, is stored in the memory 6 at addresses corresponding to the respective points.

Next, the beam is deflected by a minute angle of deflection $\Delta\phi$ and pulse beam transmission is again carried out, whereafter the average velocities Vra', Vrb', Vrc', Vrd', Vre' of points a', b', c', d', e' corresponding to the aforesaid points a, b, c, d, e are calculated and output to the tangential velocity calculator 7.

The tangential velocity calculator 7 progressively compares Vra' with Vra, Vrb' with Vrb . . . Vre' with Vre, and outputs tangential velocity distributions Vta, Vtb, . . . Vte.

The operation of the tangential velocity calculator 7 will now be explained in more detail. Defining the velocity of the moving reflective member, which may, for example, be the velocity of blood flow under observation, at point a as Vra, the real velocity (absolute vectorial velocity) as $|V|a$ and the angle between the direction of movement (direction of blood flow) and the beam as $\phi a$ (vector angle), then the velocity Vra can be calculated in the velocity calculator 5 from the well known relationship $$Vra = k|V|a \cdot \cos \phi a \quad (1)$$

where k is a constant whose value depends on the frequency of the transmitted beam, the speed of sound and the like. In the same manner, Vra' is found as $$Vra' = k|V|a' \cdot \cos(\phi a + \Delta\phi) \quad (2)$$

and this formula (2) is then compared with formula (1) in the tangential velocity calculator 7.

Here, if the deflection angle $\Delta\phi$ is small and the number of times the ultrasonic pulse beam is transmitted in the same direction is also small, then the positional and time separation between the points a and a' will be small. Therefore, by properly selecting the deflection angle $\Delta\phi$ and the number of transmissions, it is possible to assume that $|V|a$ and $|V|a'$ in formulas (1) and (2) are equal, i.e. $|V|a \simeq |V|a'$.

Then, as shown in FIG. 2, the tangential velocity calculator 7 finds the difference between formula (1) and formula (2) (i.e. determines the signal Vta') and multiplies this by $1/\Delta\phi$ so as to output the signal Vta represented by formula (4).

$$\begin{aligned} Vta' &= Vra - Vra' \\ &= k|V|a\{\cos\phi a - \cos(\phi a + \Delta\phi)\} \\ &= 2k|V|a \cdot \sin(\phi a + \Delta\phi/2) \cdot \sin(\Delta\phi/2) \\ &\simeq k\Delta\phi |V|a \cdot \sin\phi a \end{aligned} \quad (3)$$

$$\begin{aligned} Vta &= Vta' \times 1/\Delta\phi \\ &= k|V|a \cdot \sin\phi a \end{aligned} \quad (4)$$

Figure 5:
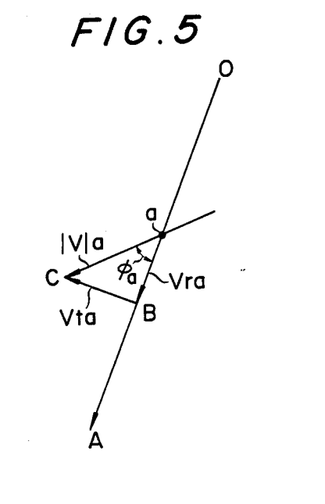
FIG. 5 is a diagram for explaining tangential velocity.

This signal Vta is the tangential velocity with respect to the velocity in the first velocity distribution and the velocity in the second velocity distribution and, as shown in FIG. 5, is the velocity component perpendicular to the direction of OA. In other words, while Vra is the radial velocity, Vta is the tangential velocity.

Next, the vector calculator 8 calculates the vectorial velocity on the basis of the tangential velocity Vta.

That is to say, using Vra, Vta of formulas (1) and (4), the absolute value calculator 8A of FIG. 3 calculates the absolute vectorial velocity $|V|a$ in accordance with the following formula (5) and the vector angle calculator 8B calculates the vector angle $\phi a$ in accordance with formula (6) below.

$$\sqrt{Vra^2 + Vta^2} = k|V|a \quad (5)$$

$$\phi a = \tan^{-1}(Vta/Vra) \quad (6)$$

This absolute vectorial velocity $|V|a$ is the actual velocity of the moving reflective member at point a, while the vector angle indicates the direction of the movement. By this vectorial velocity, therefore, it is possible to obtain accurate information regarding the movement condition.

The vectorial velocity calculation is then carried out for each of the points b . . . e (thereby obtaining the velocity distribution) and thereafter similarly for like points as the angle of deflection is progressively changed by slight increments to $2\Delta\phi$, $3\Delta\phi$, . . . . As a result, the vectorial velocities of the region of movement are obtained over the entire sector image.

Figure 6:
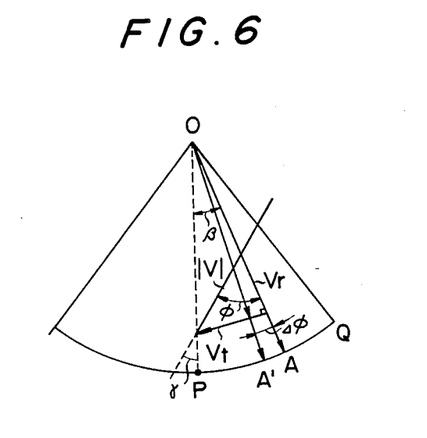
FIG. 6 is a diagram for explaining the relationship among tangential velocity, radial velocity and vectorial velocity.

Further, as shown in FIG. 6, in this first embodiment the vector angle is converted to a vector angle $\gamma$ with respect to the center scanning line OP. The vector angle $\gamma$ is obtained by subtracting the scanning angle $\beta$ from the aforesaid $\phi$ $$\gamma = \phi - \beta \quad (7)$$

The scanning angle $\beta$ is the scanning address data supplied from electronic scanner 2. After this address data has been read, the vector angle can be converted by computation to a vector angle using the center scanning line as a reference. In this connection, however, it should be noted that instead of the center scanning line it is alternatively possible to use the edge OQ of the scanned sector as the reference.

The output of the vector calculator 8 is sent to the display 30 and the vectorial velocity is written into a DSC (digital scan converter) in the display, whereafter it is displayed on the CRT.

In this case, by mapping the vectorial values in ROM at addresses represented by the computations according to the formulas (4), (5), (6), etc., the calculation of the vectorial velocities can be carried out easily and at high speed.

A second embodiment of the invention employing the autocorrelation method will now be explained with reference to FIGS. 7 and 8.

Figure 7:
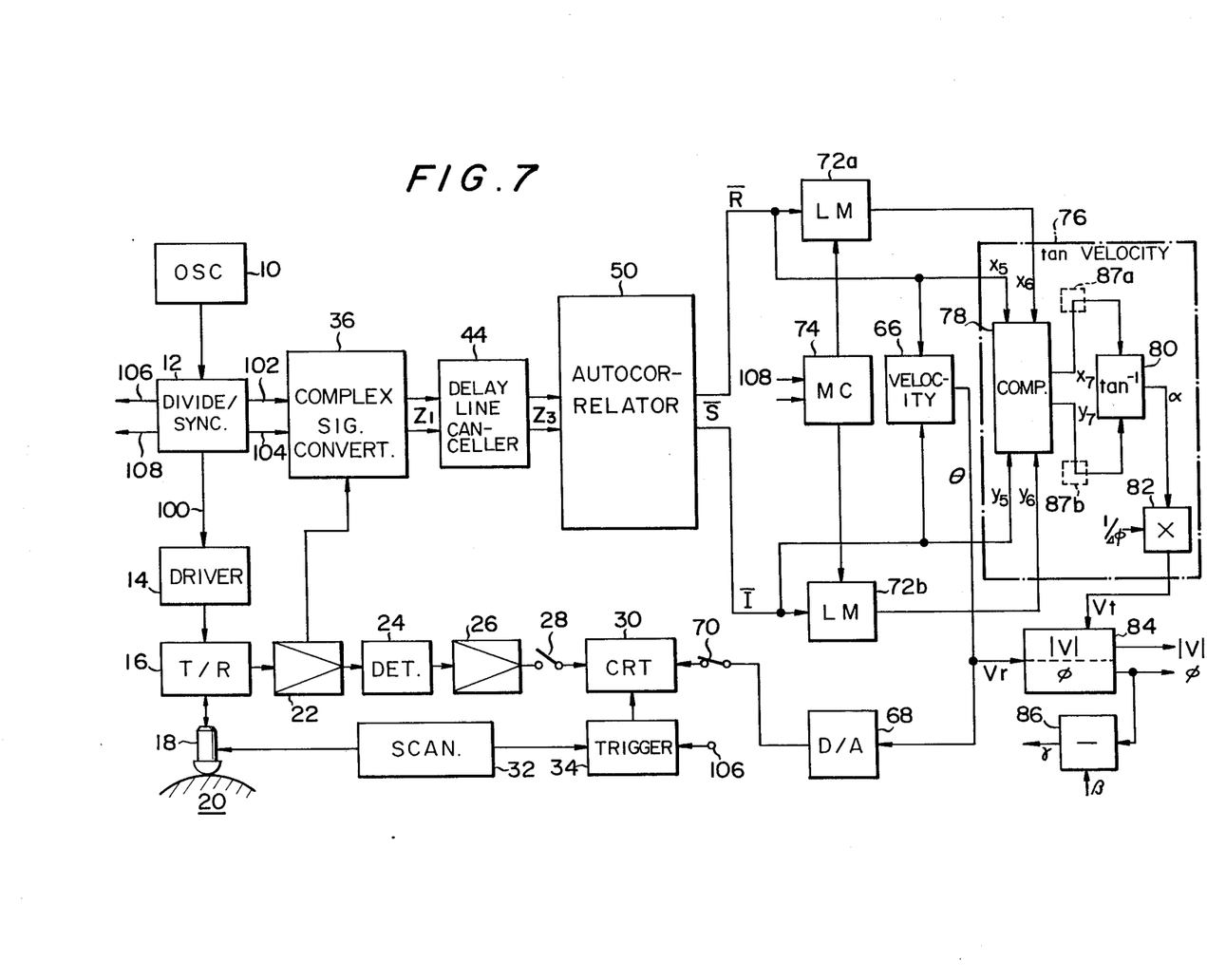
FIG. 7 is a block circuit diagram of a second embodiment of the ultrasonic Doppler diagnostic apparatus according to the invention.

Referring to FIG. 7, a crystal oscillator 10 produces a stable high frequency signal which is forwarded to a frequency divider and sync generator 12 for producing a number of output signals of desired frequencies. These output signals include a pulse rate signal 100 used for transmission of an ultrasonic pulse beam, complex reference signals 102, 104 for complex conversion, a sweep synchronization signal 106 for use in displaying the results of the ultrasonic diagnosis, and a clock signal 108 for synchronizing the various sections of the apparatus. The complex reference signals 102, 104 are of frequencies which are integer multiples of the pulse rate signal 100 and are phase-shifted from one another, by 90° in this embodiment, so as to be in a complex relationship.

The transmission signal 100 is supplied to a probe 18 through a driver 14 and a duplexer 16 and upon being excited by this signal, the probe 18 transmits an ultrasonic pulse beam into the subject under observation 20.

The echo from the subject 20 is converted into an electrical signal by the probe 18 and is forwarded through the duplexer 16 to a high frequency amplifier 22 by which it is amplified to a prescribed degree and output in two separate directions. One of the outputs goes to a display section as an ordinary B-mode or M-mode display signal.

The signal output from the high frequency amplifier 22 for carrying out ordinary B-mode or M-mode display is supplied to a CRT display 30 via a detector 24, a video amplifier 26 and a switch 28, where it is used for brightness modulation of the CRT picture.

A scanning controller 32 is provided for angularly deflecting the ultrasonic pulse beam from the probe 18, either mechanically or electrically, so as to periodically scan the subject 20, or for halting the scanning operation at a desired deflection angle. This scanning position signal from the scanning controller 32 and the sweep synchronizing signal 106 from the frequency divider and sync generator 12 are supplied to a sweep trigger pulse generator 34 to sweep-control the CRT display 30.

The other output from the high frequency amplifier 22 is subjected to autocorrelation processing. For this purpose, the Doppler signal output by the high frequency amplifier is forwarded to a complex signal converter 36 for conversion into a complex signal.

Figure 8:
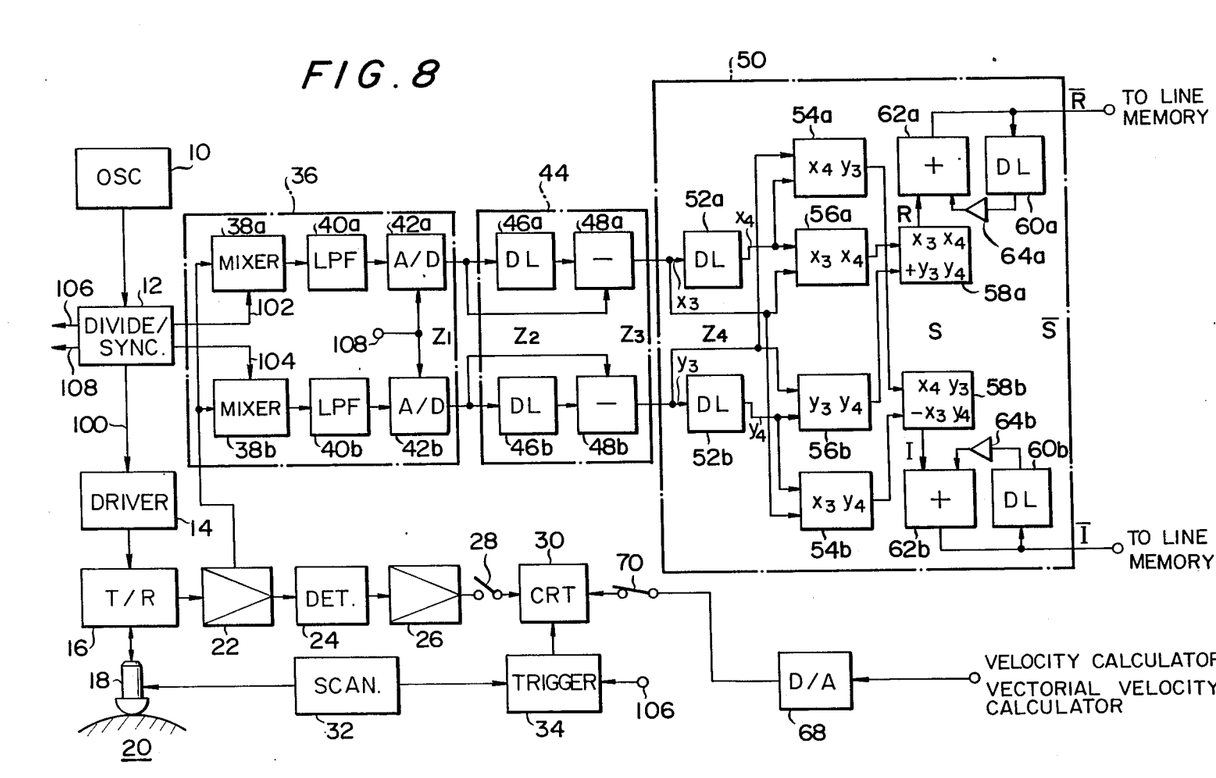
FIG. 8 is a block diagram showing the circuit arrangement of the second embodiment up to the point where the autocorrelation signal is obtained.

More specifically, as shown in FIG. 8, the complex signal converter 36 comprises a pair of mixers 38a, 38b, each of which includes a phase detector. The above received high frequency signal is processed with the complex reference signals 102, 104 in the respective mixers 38 and since the complex reference signals 102, 104 are in a complex relationship, namely since they are 90° out of phase, it is possible to obtain from the mixers 38 complex signal outputs corresponding to the received high frequency signal. More precisely, by means of mixing and detection, each of the mixers 38 outputs two signals, one with a frequency equal to the sum of and the other with a frequency equal to the difference between the frequencies of the received high frequency signal and the complex reference signal. The outputs of the mixers are then forwarded to low pass filters 40a, 40b which pass only the difference frequency component of each.

Thus, as a result of the mixing and detection operation carried out by the aforesaid mixers 38, the complex reference signals 102, 104 are single-frequency continuous waves, whereas the input signal, namely the received high frequency signal, is a pulse wave including Doppler information. As a result, the outputs from the low pass filters 40 include a large number of spectral components. This complex conversion will now be explained through the use of conversion formulas.

The complex reference signal 102 has a frequency fo which is an integer multiple of the frequency fr of the pulse rate signal 100 for the high frequency transmission signal and if the amplitude of this complex reference signal 102 is taken as 1, then it can be represented as the following sine wave voltage signal $$\sin 2\pi f o t \tag{8}$$

On the other hand, if the transmission frequency is taken as fd, then the high frequency signal received by the probe 18 can be expressed as $$\sin (2\pi f o t + 2\pi f d t) \tag{9}$$

where fd is the Doppler shift frequency.

Although, in general terms, this received signal includes the spectrum $$\sin \{2\pi(fo \pm nfr)t + 2\pi fd(1 \pm nfr/fo)t\}$$

(where fr is the frequency of the pulse rate signal and n is a natural number such as 0, 1, 2 . . . ), in order to simplify the explanation, only the spectrum in the case where n=0 in formula (9) will be considered in the following.

As the product of the complex reference signal 102 and the received high frequency signal is obtained in the mixer 38a, it is possible to derive the output expressed as the following formula which is equal to twice the product of formulas (8) and (9).

$$\cos 2\pi f d t - \cos (4\pi f o t + 2\pi f d t)$$

Then, since the frequency 2fo+fd is eliminated from this output by the low pass filter 40a, the output signal becomes $$\cos 2\pi f d t \tag{10}$$

On the other hand, since the complex reference signal 104 is out of phase by 90° with the signal 102, it can be expressed as the following cosine voltage signal $$\cos 2\pi f o t \tag{11}$$

and the aforesaid signal is mixed and detected in the mixer 38b and then passed through the filter 40b to be converted to $$\sin 2\pi f d t \tag{12}$$

thus producing a complex signal having a real component as represented by formula (10) and an imaginary component as represented by the formula (12). These signals can be expressed by the following complex formula $$Z_1 = \cos 2\pi f d t + i \sin 2\pi f d t \tag{13}$$

The signals $Z_1$ thus obtained by complex conversion are then converted to digital signals by A/D converters 42a, 42b, whereafter they are forwarded to a complex delay-line canceler 44. The clock signal 108 is supplied to the A/D converters 42 where it is used to carry out sampling.

As this second embodiment is provided with the complex delay-line canceler 44, it is possible to eliminate the portions of the signal received from the stationary or slow moving members within the living organism (the subject) and to obtain velocity signals for only the moving portions, thus realizing a great improvement in the quality of the video signal.

The delay-line canceler 44 has a pair of delay lines 46a, 46b each of which has a delay time equal to one period T of the pulse rate signal. These delay lines may, for example, be constituted of a number of memories or shift registers equal to the number of clock pulses per one period T. The delay lines 46a, 46b are connected with subtracters 48a, 48b which successively compare the inputs to the delay lines 46a, 46b (i.e. the signals during the current period T) with the outputs thereof (i.e. the signals during the preceding period T) at the same depth and calculate the difference between consecutive periods T. Therefore, since in the case of the echo signals from the stationary and slow moving parts of a living organism there is little or no difference between the current and preceding periods, the output of the subtracters 48a, 48b approaches zero, and, on the other hand, the signals for the high velocity portions, for example blood flow signals, are obtained as large outputs. Thus, echo signals from stationary and slow moving parts of the living organism (so-called clutter) can be suppressed.

The operation of the complex delay-line canceler 44 will now be explained with reference to the following formulas. Although in FIG. 8, digital signals are input to the delay-line canceler 44, for simplicity of explanation, the following discussion will be based on the analog signals represented by formula (13). When the input signals $Z_1$ applied to the delay lines 46 are represented by formula (13), the output $Z_2$ delayed by one period becomes $$Z_2 = \cos 2\pi fd(t-T) + i \sin 2\pi fd(t-T) \quad (14)$$

As a result the difference outputs of the subtracters 48 become $$Z_3 = Z_1 - Z_2 = -2 \sin 2\pi fd(T/2) \cdot \sin 2\pi fd\{t-(T/2)\} + i2 \sin 2\pi fd(T/2) \cdot \cos 2\pi fd\{t-(T/2)\}$$

and if the difference output $Z_3$ is expressed as $$Z_3 = x_3 + iy_3$$

then $x_3$, $Y_3$ can be obtained as follows $$x_3 = -2 \sin 2\pi fd(T/2) \cdot \sin 2\pi fd\{t-(T/2)\} \quad (15)$$

$$Y_3 = 2 \sin 2\pi fd(T/2) \cdot \cos 2\pi fd\{t-(T/2)\} \quad (16)$$

Therefore, in accordance with the above, the signals $x_3$, $Y_3$ are obtained as outputs from the subtracters 48a, 48b, respectively.

The complex signals from which the low velocity signal components have been eliminated as described above are then processed by an autocorrelator 50 in order to obtain the autocorrelation of the signals $Z_3$ having a delay of T.

First the signals $Z_3$ are input to delay lines 52a, 52b by which they are delayed by one period to produce signals $Z_4$ as expressed by the following formulas $$Z_4 = x_4 + iy_4$$

$$x_4 = -2 \sin 2\pi fd(T/2) \cdot \sin 2\pi fd\{t-(3/2T)\} \quad (17)$$

$$y_4 = 2 \sin 2\pi fd(T/2) \cdot \cos 2\pi fd\{t-(3/2T)\} \quad (18)$$

Then, finding the conjugate signal $Z_4^*$ of the signal $Z_4$ as $Z_4^* = x_4 - iy_4$ and calculating the conjugate of $Z_3$ and $Z_4$ by the following formula, the autocorrelation is found $$Z_3 Z_4^* = (x_3 + iy_3)(x_4 - iy_4) = x_3 x_4 + y_3 y_4 + i(x_4 y_3 - x_3 y_4)$$

In order to obtain this correlation, the autocorrelator 50 is provided with four multipliers 54a, 54b, 56a, and 56b and with two adder-subtracters 58a, 58b.

If the output of the adder-subtracter 58a is taken as R, then from the preceding formulas (15), (16), (17) and (18), we obtain $$R = x_3 x_4 + y_3 y_4 = 4 \sin^2 2\pi fd(T/2) \cos 2\pi fdT \quad (19)$$

And if the output of the adder-subtracter 58b is taken as I, we obtain $$I = x_4 Y_3 - x_3 y_4 = 4 \sin^2 2\pi fd(T/2) \sin 2\pi fdT \quad (20)$$

Then by combining the outputs from the two adder-subtracters, the following is obtained $$S = R + iI \quad (21)$$

Next, as this output S contains the variable signal components and the noise from the apparatus, it is averaged by an averaging circuit for elimination of such extraneous components. The average is expressed by $\overline{S} = \overline{R} + i\overline{I}$, whereby the complex correlation is obtained.

In the averaging circuit, delay lines 60a, 60b produce outputs delayed by one period and these outputs are added with the inputs for the current period in adder-subtracters 62a, 62b, whereafter the outputs obtined are fed back to the delay lines 60a, 60b and the operation is repeated. If a digital circuit is used for this addition, the average value can be obtained merely by outputting the higher order bit of the added output. However, if this operation is simply repeated, the magnitude of the output will successively increase with the increasing number of additions until at last saturation is reached. Because of this, this embodiment is provided with weighting circuits 64a, 64b for attenuating the outputs before adding them to the inputs. More specifically, by defining the amount of attenuation as $\alpha$, the signal for ten periods earlier, for example, is attenuated by a factor of $\alpha^{10}$ relative to the signal for the current period before being added to the signal for the current period. Thus the effect on the output is made small, so that an averaging effect like that of a low pass filter or a running average circuit can be obtained. Moreover, by changing the amount of weighting by the weighting circuits 64a, 64b, it is possible to adjust the degree of averaging.

Thus as described in the foregoing, in this second embodiment the autocorrelations are obtained by calculating the conjugates of the complex signals and, as shown in FIG. 7, the correlation outputs are input to a velocity calculator 66 which uses them to obtain the argument $\theta$ of the correlation outputs $\overline{S}$. More specifically, the argument $\theta$ is obtained from the formulas (19) and (20) as follows $$\theta = \tan^{-1}(\overline{I}/\overline{R}) = 2\pi fdT \quad (22)$$

As a result, the Doppler shift frequency $\overline{f}d$ can be easily obtained from the argument $\theta$ as follows $$\overline{fd} = \theta/2\pi T \quad (23)$$

What characterizes the present invention is that the autocorrelations of two received signals having a slight difference in deflection angle are compared so as to obtain the tangential velocity at a given distance and that the vectorial velocity is calculated from this tangential velocity. For this purpose, there are provided, in addition to the autocorrelator 50 and the like, the line memories 72a, 72b for storing the autocorrelation signal of a first received signal for a first cycle, the tangential velocity calculator 76 for comparing the autocorrelation signal of the first received signal and the autocorrelation signal of a second received signal and calculating the tangential velocity, and a vectorial velocity calculator 84 for carrying out vector calculation on the basis of the output of the tangential velocity calculator 76.

The tangential velocity calculator 76 is constituted of a comparator 78, an inverse tangent calculator 80, and a multiplier 82 for multiplication by $1/\Delta\phi$. In this embodiment, the comparator 78 is constituted of the multipliers 54, 56 used in the autocorrelator 50 for calculating the conjugate product plus the subtracter 58, which is also a component of the autocorrelator 50, and carries out the same operations as these.

An explanation will now be made on how the embodiment of the aforesaid arrangement carries out the operations between the calculation of tangential velocity and the calculation of vectorial velocity.

The outputs $\bar{R}$ and $\bar{I}$ of the autocorrelator 50 can be represented by the following formulas, and are forwarded to the line memories 72a, 72b, respectively.

$$\bar{R} = |R| \cos \theta \qquad (24)$$

$$\bar{I} = |R| \sin \theta \qquad (25)$$

Here, $\bar{R}$ and $\bar{I}$ are the final values from the autocorrelator 50 and are the averages of signals obtained by several transmissions of the ultrasonic pulses in a given direction. Further, the argument $\theta$ includes a velocity signal and, if the angle between the direction of the ultrasonic beam and the direction of movement is defined as $\phi$, can be written as $$\theta = kV \cos \phi \qquad (26)$$

B-mode scanning is carried out in the same manner in the first and second embodiments. As illustrated in FIG. 6, the echo signal from the O→A direction forms a first received signal formed of a pulse train, while the pulse train of the echo signal from the O→A' direction constitutes a second received signal.

Of the autocorrelation signals obtained from the first received signal, the $\bar{R}$ signal is stored in the line memory 72a and the $\bar{I}$ signal is stored in the line memory 72b, while the memory controller 74 controls memory read and write on the basis of clock pulses and scanning address signals it receives.

The autocorrelation signal obtained from the second received signal is sent directly to the comparator 78 without being passed through the line memory 72 and is also written into the line memory 72 in preparation for the next calculation. The first and second autocorrelation signals are compared in the comparator 78. Here, defining the first autocorrelation signal as $\bar{S}a$ and the second autocorrelation signal as $\bar{S}b$, these can be represented by the following formulas.

$$\bar{S}a = |R| \cos (kV \cos \phi) + i|R| \sin (kV \cos \phi) \qquad (27)$$

$$\bar{S}b = |R| \cos [kV \cos (\phi - \Delta\phi)] + i|R| \sin [kV \cos (\phi - \Delta\phi)] \qquad (28)$$

These two signals are compared in the comparator 78 through calculation of their conjugates. The comparator 78 is constituted by an arrangement the same as that of the multipliers 54, 56 and the subtracter 58 shown in FIG. 8. As input it receives $\bar{S}a$, $\bar{S}b$ (corresponding to $Z_3$, $Z_4$) and outputs $x_7$, $y_7$ (corresponding to R, I). $x_7$, $y_7$ represent the following tangential velocity component signals.

$$\begin{aligned} x_7 &= |R|^2 \cos[kV\{\cos\phi - \cos(\phi - \Delta\phi)\}] \\ &= |R|^2 \cos(kV\Delta\phi \sin\phi) \end{aligned} \qquad (29)$$

$$y_7 = -|R|^2 \sin (kV\Delta\phi \sin \phi) \qquad (30)$$

The signals $x_7$, $y_7$ are sent to the inverse tangent calculator 80 where they are used to calculate the tangent angle $\alpha$ as $$\alpha = -\tan^{-1} y_7/x_7 = kV\Delta\phi \sin \phi \qquad (31)$$

Here by inserting between the comparator 78 and the inverse tangent calculator 80 multipliers 88a, 88b constituted by the delay lines 60, the adders 62 and the weighting circuits 64 shown in FIG. 8, it is possible to eliminate noise components and carry out measurement with high accuracy.

In the multiplier 82, since the minute deflection in scanning angle $\Delta\phi$ is constant, the tangent angle $\alpha$ is multiplied by the reciprocal of $\Delta\phi$, namely $1/\Delta\phi$. Therefore, the output of the multiplier 82 becomes $$Vt = kV \sin \phi \qquad (32)$$

where Vt represents the tangential velocity.

Then, defining the output of the velocity calculator 66 as Vr, we have $$Vr = kV \cos \phi \qquad (33)$$

As Vr represents the radial velocity, it is possible from this and the tangential velocity Vt to calculate the vectorial velocity V.

The vectorial velocity calculator 84 calculates the absolute vectorial velocity as $$|V| = \sqrt{Vt^2 + Vr^2} = kV \qquad (34)$$

And the vector angle is obtained as $$\phi = \tan^{-1} (Vt/Vr) \qquad (35)$$

The absolute value $|V|$ represents the actual velocity of the moving reflective member in the O→A direction, while the vector angle $\phi$ represents the direction of this movement. Thus from the vectorial velocity it is possible to obtain accurate information regarding the state of movement.

Conversion to vector angle $\gamma$ with respect to the center scanning line OP is carried out as shown in FIG. 6 also in this second embodiment. Namely, the scanning angle $\beta$ is subtracted from the angle $\phi$ in a subtracter 86 to obtain $\gamma$ as $$\gamma = \phi - \beta \qquad (36)$$

This scanning angle $\beta$ is the scanning address supplied by the scanning controller 32. After this address data has been read, the vector angle can be converted by computation to a vector angle with reference to the center scanning line. Alternatively it is possible to use the scanning start line O-Q as the reference.

The scanning angle is thereafter progressively deflected in small increments to $2\Delta\phi$, $3\Delta\phi$, ... and at each deflected position the tangential velocity calculation is similarly carried out. As a result, the vectorial velocity distribution for the moving member is obtained over the entire sector being scanned.

The output of the vector calculator 84 is sent to the display 30 and the vectorial velocity is written into a DSC (digital scan converter) in a display, wereafter it is displayed on the CRT.

Figure 9:
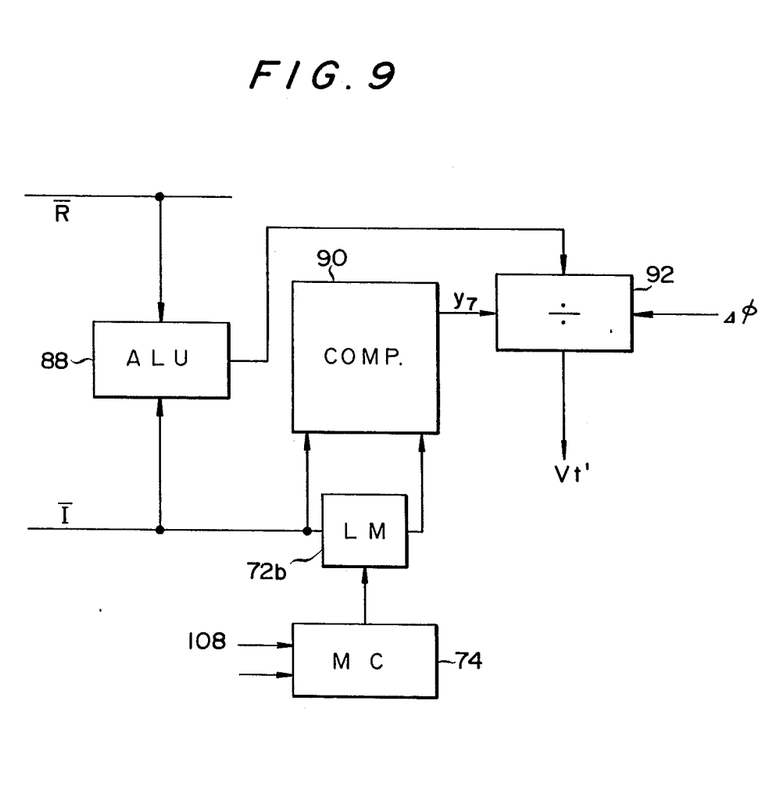
FIG. 9 is a block diagram showing the circuit of a tangential velocity calculator in the second embodiment of the invention.

Next, an example of the tangential velocity calculator will be explained with reference to FIG. 9.

In this example, the deflection angle $\Delta\phi$ is set to about 1° to obtain a small value for $x_7$ in formula (29) and the tangential velocity is calculated from $y_7$ in formula (30). More specifically, the tangential velocity calculator 76 is provided with an arithmetic processor 88, a comparator 90 and a divider 92, and the arithmetic processor 88 carries out calculations in accordance with the following formula derived from the aforesaid formulas (24) and (25)

$$\bar{R}^2 + \bar{I}^2 = |R|^2$$

Further, the comparator 90 is constituted of the circuit components of the aforesaid comparator 78 used for processing y5, y6, i.e. is constituted of the multipliers 54a, 54b and the subtracter 58b shown in FIG. 8. Therefore, although the comparator 90 outputs the same y7 as that in formula (30), since $\Delta\phi$ is small, it is possible to write $$y_7 \delta - |R|^2 kV\Delta\phi \sin\phi$$

Further, the divider 92 uses the output of the arithmetic processor 88 and the small deflection angle to calculate the tangential velocity Vt' as $$Vt' = -\bar{R}^2 kV\Delta\phi \sin\phi \div (-\bar{R}^2\Delta\phi) = kV \sin\phi$$

From the tangential velocity Vt' calculated in this way it is possible to obtain the absolute vectorial value in the manner described earlier. A particular advantage of the arrangement just described by way of example is that it enables determination of the vectorial velocity with a simple device in cases where a particularly high degree of computation accuracy is not required.

The ultrasonic Doppler apparatus described in the foregoing can be applied in the case of B-mode display involving two-dimensional step scanning as well as in the case of a moving target indicator device, and further enables a display to be overlaid on an image of a subject cross-section.

The vectorial velocity signal obtained as described above is converted to an analog voltage signal by a D/A converter 68, whereafter it is sent to the CRT display 30 via a switch 70 and used as a brightness modulation signal for displaying a B-mode picture of the movement velocity distribution.

In this second embodiment, by operation of the switches 70 and 28 it is possible to have the CRT 30 selectively display pictures based on either the ordinary picture signal from the video amplifier 26 or the aforesaid Doppler signal and, moreover, to display both pictures simultaneously, if desired.

In accordance with the present invention, since, as described in the foregoing, the tangential velocity is obtained from velocity signals or autocorrelation signals derived from two received signals differing only slightly in deflection angle and the vertorial velocity is then obtained on the basis of the so-obtained tangential velocity, the velocity and direction of movement of a moving reflective member within the subject under observation can be detected easily and with high accuracy without need of transmitting ultrasonic beams into the subject from two separated locations.

Further, with the apparatus according to the first embodiment described, since simplified circuitry provides ease of operation, it is possible to realize extremely high cost-performance, while with the apparatus according to the second embodiment, very high accuracy velocity detection is enabled through precision detection of the tangential velocity.

As a result, the present invention makes it possible to augment the diagnostic information that has been obtainable with conventional ultrasonic diagnostic apparatuses employing the ultrasonic echo method with the additional simultaneous display of high-accuracy information relating to, for example, blood flow velocity and blood flow velocity distribution. It is believed, therefore, that the invention will make a major contribution to the quality and quantity of information available from ultrasonic Doppler diagnostic apparatuses.

What is claimed is:

1. An ultrasonic Doppler apparatus for providing data for diagnosis of the the distance and velocity of a moving member within a subject, comprising:
   means for transmitting an ultrasonic pulse beam of a given fixed pulse recurrence frequency into said subject and for receiving said beam after reflection therein;
   scanning means for sector scanning said ultrasonic pulse beam in at least two successive directions, each of said successive directions being separated by a minute deflection angle therebetween;
   means coupled to said transmitting and receiving means for deriving from said received beam at least first and second velocity distribution signals corresponding to at two of said successive directions, said velocity distribution signals being representative of the velocity of said moving members;
   memory means responsive to said velocity distribution deriving means for storing a first velocity distribution signal from among said distribution signals;
   tangential velocity calculating means responsive to said memory means and to said velocity distribution deriving means, including means for comparing said stored first velocity distribution signal with a next velocity distribution signal of said at least first and second distribution signals corresponding to a first and next of at least two successive directions, and means responsive to said comparing means and to a signal representative of said minute deflection angle for calculating a velocity distribution component in a direction tangential to an arc of a scanned sector defined by said first and next directions, and for providing an output thereof;
   whereby said tangential velocity component distribution output is representative of at least one dimension of image data for diagnosis of the distance and velocity of said moving members.

2. An ultrasonic Doppler diagonstic apparatus according to claim 1 wherein said tangential velocity calculating means calculates a vector conjugate of the autocorrelation signal.

3. An ultrasonic Doppler diagnostic apparatus according to claim 2 wherein said tangential velocity calculating means calculates the imaginary component of the conjugate.

4. An ultrasonic Doppler apparatus for providing data for diagnosis of the distance and velocity of moving members within a subject, comprising:
   means for transmitting an ultrasonic pulse beam of a given fixed pulse recurrence frequency into said subject and for receiving said beam after reflection therein;
   scanning means for sector scanning said ultrasonic pulse beam in at least two successive directions, each of said successive directions being separated by a minute deflection angle therebetween;
   autocorrelation means coupled to said transmitting and receiving means for deriving from said received beam at least first and second autocorrelation signals corresponding to said at least two successive directions, said autocorrelation signals being representative of the velocity of said moving members;

memory means responsive to said autocorrelation means for storing a first autocorrelation signal from among said autocorrelation signals;

tangential velocity calculating means responsive to said memory means and to said autocorrelation means, including means for comparing said stored first velocity autocorrelation signal with a next autocorrelation signal of said at least first and second autocorrelation signals corresponding to a first and next of at least two successive directions, and means responsive to said comparing means and to a signal representative of said minute deflection angle for calculating a velocity distribution component in a direction tangential to an arc of a scanned sector defined by said first and next directions, and for providing an output thereof;

whereby said tangential velocity component distribution output is representative of at least one dimension of image data for diagnosis of the distance and velocity of said moving members.

5. An ultrasonic Doppler diagnostic apparatus according to either one of claims 3 and 4 further comprising a calculating means for calculating vector velocity of the moving reflective member from the output of said tangential velocity calculating means.

6. An ultasonic Doppler diagnostic apparatus according to claim 5 wherein said calculating means further comprises a vector angle calculating means for calculating a vector angle in response to the scanning angle into an angle with respect to the reference direction of sector scanning.

7. An ultrasonic Doppler diagnostic apparatus according to claim 5 wherein said calculating means calculates the absolute vectorial velocity as the square root of the sum of the square of the tangential velocity obtained as the output of said tangential velocity calculating means and a square of a radial velocity of the moving reflective member from said signals representative of the velocity of said moving members.

8. An ultrasonic Doppler diagnostic apparatus according to claim 5 wherein said calculating means calculates the direction of the vectorial velocity from the inverse tangent of the quotient obtained by dividing the tangential velocity obtained as the output of said tangential velocity calculating means by a radial velocity of the moving reflective member from the said signals representative of the velocity of said moving members.

* * * * *